United States Patent [19]

Curtis et al.

[11] Patent Number: 5,209,251

[45] Date of Patent: * May 11, 1993

[54] DENTAL FLOSS

[75] Inventors: John P. Curtis, Bloomsbury; James H. Kemp, North Brunswick, both of N.J.

[73] Assignee: Colgate-Palmolive Company, New York, N.Y.

[*] Notice: The portion of the term of this patent subsequent to Jul. 23, 2008 has been disclaimed.

[21] Appl. No.: 729,834

[22] Filed: Jul. 11, 1991

Related U.S. Application Data

[63] Continuation-in-part of Ser. No. 282,962, Dec. 2, 1988, Pat. No. 5,033,488, which is a continuation-in-part of Ser. No. 174,757, Mar. 29, 1988, abandoned.

[51] Int. Cl.$^5$ .............................................. A61C 15/00
[52] U.S. Cl. ...................................................... 132/321
[58] Field of Search ............... 132/321, 322, 323, 324, 132/325, 326, 327, 328, 329; 424/50

[56] References Cited

U.S. PATENT DOCUMENTS

| | | | |
|---|---|---|---|
| 2,700,636 | 1/1955 | Ashton | 424/54 |
| 3,538,230 | 11/1970 | Pader et al. | 424/50 |
| 3,699,979 | 10/1972 | Muhler et al. | 132/321 |
| 3,771,536 | 11/1973 | Dragan | 132/321 |
| 3,800,812 | 4/1974 | Jaffe | 132/321 |
| 3,830,246 | 8/1974 | Gillings | 132/321 |
| 3,837,351 | 9/1974 | Thornton | 132/321 |
| 3,897,795 | 8/1975 | Engel | 132/321 |
| 3,943,949 | 3/1976 | Ashton et al. | 132/321 |
| 3,953,566 | 4/1976 | Gore | 264/288 |
| 3,962,153 | 6/1976 | Gore | 260/2.5 |
| 4,029,113 | 6/1977 | Guyton | 132/321 |
| 4,053,365 | 7/1977 | Klepak et al. | 132/321 |
| 4,187,390 | 2/1980 | Gore | 174/102 |
| 4,215,478 | 8/1980 | Thomas et al. | 433/25 |
| 4,256,806 | 3/1981 | Snyder | 428/378 |
| 4,304,245 | 12/1981 | Lichfield | 132/321 |
| 4,385,093 | 5/1983 | Hubis | 428/316 |
| 4,414,990 | 11/1983 | Yost | 132/321 |
| 4,478,665 | 10/1984 | Hubis | 156/229 |
| 4,645,662 | 2/1987 | Nakashima et al. | 424/50 |
| 4,776,358 | 10/1988 | Lorch | 433/216 |

Primary Examiner—John J. Wilson
Attorney, Agent, or Firm—Michael J. McGreal; Robert C. Sullivan

[57] ABSTRACT

A dental floss is produced from expanded polytetrafluoroethylene that has been coated with a friction enhancing coating such as a microcrystalline wax to increase the friction coefficient of the floss. The polytetrafluoroethylene is preferably expanded to form a structure having a plurality of nodes interconnected by fibrils. The floss has a tensile strength of at least about 10,000 psi and a weight of about 500 denier to about 1500 denier. The coefficient of friction of the wax coated floss ranges from about 0.08 to 0.25. The floss may be comprised of a single strand or multiple strands. The floss may contain an optional dentifrice or pharmaceutically active material for delivery to the tooth and gum surfaces during use.

20 Claims, No Drawings

DENTAL FLOSS

CROSS REFERENCE TO RELATED APPLICATION

This is a continuation-in-part application of U.S. application Ser. No. 282,962 filed Dec. 2, 1988, now U.S. Pat. No. 5,033,488, which is a continuation-in-part of U.S. application Ser. No. 174,757 filed Mar. 29, 1988, now abandoned.

FIELD OF THE INVENTION

The present invention relates to dental flosses produced from expanded polytetrafluoroethylene having a friction coating to increase the friction coefficient of the floss and to enhance handling characteristics of the floss. More particularly the invention is directed to single stranded expanded polytetrafluoroethylene dental flosses and multi-stranded expanded polytetrafluoroethylene dental flosses.

BACKGROUND OF THE INVENTION

Dental flosses have long been used effectively to clean the spaces between the teeth and under the gum margin. One example of a dental floss is disclosed in U.S. Pat. No. 3,800,812. To increase the effectiveness of the floss, some flosses have included certain medicinal ingredients such as fluoride compounds to protect the tooth enamel from acid attack. Bactericides have also been used in connection with dental floss to inhibit periodontal disease. The medicinal components have typically been applied as a coating to the preformed dental floss.

When used properly, dental floss has been found to be effective in inhibiting tooth decay and gum disease and is recommended by dentists in the daily dental hygiene program. Dental floss often has the disadvantage of causing the gums to bleed, which discourages its use by some people. Bleeding of the gums may be caused by the friction of the floss against the gum surface and by the rough texture of the floss.

There have been numerous attempts in the art to produce a superior dental floss that is convenient to use and is less prone to cause bleeding of the gums. Other dental flosses have been provided with a dentifrice component. For example, U.S. Pat. No. 3,830,246, U.S. Pat. No. 3,897,795, U.S. Pat. No. 4,215,478 and U.S. Pat. No. 3,771,536 disclose dental flosses which are impregnated with a fluoride compound to aid in the delivery of the fluoride to the tooth surface between adjacent teeth. U.S. Pat. No. 4,033,365 discloses a floss designed to retain flavorants over a long period of time through the use of non-wax polymeric coatings containing spray-dried flavor particles.

U.S Pat. No. 3,943,949 discloses a dental floss-like material in the form of a bundle of natural or synthetic fibers, such as nylon. The floss is coated with various waxes, including microcrystalline wax, to reduce the friction of the floss against the tooth surface. The wax coating is disclosed as containing a spray-dried flavorant to be dispersed during use.

As exemplified by the above-noted patents, flossing is an extremely important adjunct to proper dental hygiene. Many of the dental flosses presently on the market have received limited consumer acceptance. The lack of consumer acceptance of any single dental floss on the market is due in part to the propensity of dental floss to cause gingival bleeding. In addition, dental floss is generally considered difficult and uncomfortable to use. The consumer dissatisfaction with some dental flosses is caused by the relatively high coefficient of friction (COF) of the floss.

Because prior art flosses have such high friction coefficients, the user must apply substantial downward force to pull the floss between the contact points of the teeth. Unfortunately, the typical user will pull downward with sufficient force to allow the floss to pass between the teeth and snap against the gum surface, causing irritation and possible bleeding of the gum tissue. Some of the difficulty in pulling the floss between the teeth is the result of the thickness of the floss compared to the spaces between the teeth. In order to reduce the risk of gum injury, many manufacturers have coated the floss with wax or other lubricant to reduce the friction coefficient and increase the ease with which it can be inserted between the teeth.

SUMMARY OF THE INVENTION

The present invention is directed to dental flosses having a friction coefficient that is less than conventional dental flosses to enable the user to insert the floss between tight spaces between the teeth with reduced risk of injury to the user. Although the dental floss has a reduced friction coefficient, the floss is effective in cleaning the tooth surfaces above and below the gum line.

The dental floss of the invention is produced from polytetrafluoroethylene in the form of a strand. In the preferred embodiment, the floss is polytetrafluoroethylene which has been expanded at an elevated temperature. The extremely low friction coefficient of polytetrafluoroethylene, however, makes it difficult to handle by the user. In order to increase the ease of handling, a coating of a composition capable of increasing the coefficient of friction is applied to the floss which results in an increase in the friction coefficient of the floss. In a preferred form of the invention, the coating is a wax and particularly a wax coating of a microcrystalline wax. The wax should also be of a low to medium molecular weight.

The floss is produced from polytetrafluoroethylene that has been stretched at elevated temperatures. The resulting polytetrafluoroethylene has a highly porous structure consisting of nodes interconnected by very small fibrils. The size of the floss as it is to be used may range from about 500 denier to about 1500 denier and, preferably, about 600 denier to about 1200 denier. The floss has a tensile strength greater than about 10,000 psi and a polymeric matrix strength of at least about 100,000 psi.

The individual polytetrafluoroethylene strands can be of a denier of about 100 denier to about 1500 denier. When the strand denier is less than about 600 denier, the floss usually will be a multi-stranded floss. That is about 2 to 12 strands of the floss will be used, usually in a lightly twisted condition in order to form the strands into a cohesive single thread. In multi-stranded polytetrafluoroethylene flosses the wax will serve two purposes. One purpose is to maintain the individual strands in the twisted single thread shape. A second is to increase the coefficient of friction to about 0.08 to 0.25.

In one preferred embodiment, a strand of the expanded polytetrafluoroethylene is immersed in a bath of a microcrystalline wax either in a molten condition or dispersed in an organic solvent or carrier. The strand is removed from the bath, and when a solvent is used, dried to remove the solvent. In use, the wax coating provides a sufficient friction coefficient to be easily handled by the user. It will also hold multi-stranded flosses in a single thread form. When the coated floss is inserted between the teeth, the wax coating tends to be removed as the floss is pulled between the contact points of adjacent teeth to expose the polytetrafluoroethylene and allow ease of insertion between the teeth. A thinner floss of 600 or 800 denier is particularly easy to use and provides sufficient tensile strength to resist breakage.

In another preferred embodiment multiple strands of the expanded polytetrafluoroethylene are immersed in the molten or emulsion wax bath. Either just prior to, within, or just after the wax bath the strands are lightly twisted to form a single thread. The twisted strands are then cooled to maintain the strands in a twisted state.

In a further preferred embodiment, the floss is coated or impregnated with a bioactive component. The dentifrice or bioactive component may be applied to the floss before coating with the wax or may be dispersed in the wax and applied simultaneously.

DETAILED DESCRIPTION OF THE INVENTION

Many of the disadvantages and limitations of the previous dental floss materials are overcome by the present invention while producing a dental floss that is convenient to use. The dental flosses of the present invention are sufficiently strong to be used without breakage and have a friction coefficient substantially less than conventional dental floss.

The dental floss of the invention is produced from polytetrafluoroethylene to provide a floss with a low friction coefficient. Conventionally produced polytetrafluoroethylene has a low tensile strength, a tendency to readily stretch under tension, and is generally not suitable as a dental floss. It has been found that dental floss of sufficient strength can be produced from expanded polytetrafluoroethylene. The polytetrafluoroethylene in a preferred embodiment is produced according to the methods disclosed in U.S. Pat. No. 3,953,566 and U.S. Pat. No. 3,962,153 to W. L. Gore & Associates, which patents are hereby incorporated by reference. The floss strands are produced by paste-forming techniques where the polymer is converted to a paste and shaped into a strip which is then expanded by stretching in one or more directions. While it is held in the stretched condition, it is heated to at least 327° C., after which it is cooled. This strip is then cut to form different denier floss strands.

The sheet or tape from which the floss strands are produced can be produced by various techniques. Extrusions of various cross-sectional shapes such as tubes, rods and tapes are commonly obtained from a variety of polytetrafluoroethylene resins. Paste-forming operations, such as calendaring and molding, are also practiced commercially to obtain the desired shapes. The steps in paste-forming processes include mixing the resin with a lubricant such as odorless mineral spirits, and carrying out forming steps in which the resin is subjected to shear, thus making the shaped articles cohesive. The lubricant is removed from the extruded shape usually by drying. If this unsintered product is heated above the polymer's melting point, generally about 327° C., it will sinter or coalesce into an essentially impermeable structure and not be effective to make a floss.

Rather the paste-formed, dried, unsintered shapes should be expanded by stretching them in one or more directions under certain conditions so that they become substantially much more porous and stronger. This phenomenon of expansion with a resulting increase in strength occurs with certain preferred polytetrafluoroethylene resins and within preferred ranges of rate of stretching and preferred ranges of temperature. The preferred temperature range is from 35° C. to 327° C. At the lower temperatures within this range it has been found that there is a maximum rate of expansion beyond which fracture occurs, as well as a lower limit beneath which fracture also occurs or where weak materials are obtained. The lower limit is of much more practical significance. At high temperatures within this range, only the lower limit of the expansion rate has been detected. The lower limit of expansion rates interact with temperature in a roughly logarithmic fashion, being much higher at higher temperatures. Most, but not all, of the desirable products are obtained when expansion is carried out at the higher temperatures within the range of 35° C. to 327° C. The balance of orientation in the extruded shape also affects the relationship between the proper range of expansion rates and temperature. It is found that some resins are much more suitable for the expansion process than others, since they can be processed over a wider range of rate and temperature and still produce useful products. The primary requisite of a suitable resin is a very high degree of crystallinity, preferably in the range of 98% or above, and correspondingly low amorphous content. It has been found that techniques for increasing the crystallinity, such as annealing at high temperatures just below the melt point, improve the performance of the resin in the expansion process. Copolymers of polytetrafluoroethylene, which have defects in the crystalline structure that introduce a higher amorphous content, do not work as well as homopolymers. However, it is found, for example, that resins which contain less than 0.2% of hexafluoropropylene as a comonomer can be made to work in this invention by going to very high rates of expansion at high temperatures just below the melting point.

The porous microstructure of the expanded material is affected by the temperature and the rate at which it is expanded. The structure consists of nodes interconnected by very small fibrils. In the case of uniaxial expansion the nodes are elongated, the longer axis of a node being oriented perpendicular to the direction of expansion. The fibrils which interconnect the nodes are oriented parallel to the direction of expansion. These fibrils appear to be characteristically wide and thin in cross-section, the maximum width being equal to about 0.1 micron (1000 angstroms) which is the diameter of the crystalline particles. The minimum width may be 1 or 2 molecular diameters or in the range of 5 or 10 angstroms. The nodes may vary in size from about 400 microns to less than a micron, depending on the conditions used in the expansion. Products which have been expanded at high temperatures and high rates have a more homogeneous structure, i.e., they have smaller, more closely spaced nodes and these nodes are interconnected with a greater number of fibrils. These products are also found to have much greater strength. The expansion process results in a tremendous increase in the tensile strength of the polytetrafluoroethylene and an increase in the porosity.

The increase in strength of the polymer matrix is dependent upon the strength of the extruded material before expansion, the degree of crystallinity of the polymer, the rate and temperature at which the expansion is performed, and amorphous locking. When all these factors are employed to maximize the strength of the material, tensile strength of 10,000 psi and above with porosity of 90% or more are obtained. In these cases the polymeric matrix has strengths in excess of 100,000 psi. In contrast, the maximum tensile strength of conventional extruded or molded polytetrafluoroethylene after sintering is generally considered to be about 3,000 psi, and for conventional extruded and calendared polytetrafluoroethylene tape which has been sintered the maximum is about 5,100 psi. Porous polytetrafluoroethylene shaped articles have been produced by stretching to lengths exceeding 1500 times the original sample length. Useful products have been produced by stretching samples in the range of a few hundred percent to greater than 50 times the original sample length.

By definition, the tensile strength of a material is the maximum tensile stress, expressed in force per unit cross-sectional area of the specimen, which the specimen will withstand without breaking (see, for example, The American Society for Testing and Materials, "1970 Annual Book of ASTM Standards—Part 24," at p. 41). For porous materials, the cross-sectional area of solid polymer within the polymeric matrix is not the cross-sectional area of the porous specimen, but is equivalent to the cross-sectional area of the porous specimen multiplied by the fraction of solid polymer within that cross-section. This fraction of solid polymer within the cross-section is equivalent to the ratio of the specific gravity of the porous specimen itself divided by the specific gravity of the solid polymeric material which makes up the porous matrix. Thus, to compute matrix tensile strength of a porous specimen, one divides the maximum force required to break the sample by the cross-sectional area of the porous sample, and then multiplies this quantity by the ratio of the specific gravity of the solid polymer divided by the specific gravity of the porous specimen. Equivalently, the matrix tensile strength is obtained by multiplying the tensile strength computed according to the above definition by the ratio of the specific gravities of the solid polymer to the porous product.

The expanded polytetrafluoroethylene generally has a coefficient of friction of less than about 0.08. Conventional dental flosses produced from nylon have a coefficient of friction of about 0.2. The uncoated, expanded polytetrafluoroethylene has been found to be effective as a dental floss and easily slides through close spaces between the teeth. The low coefficient of friction of polytetrafluoroethylene reduces injury and trauma to the gum tissue even at thickness of as low as 500 denier. The uncoated polytetrafluoroethylene floss has, however, been found to be difficult to handle due to the extremely low coefficient of friction of the polytetrafluoroethylene. It has been found that the polytetrafluoroethylene floss can be coated or otherwise treated with a friction coating, such as a wax, to increase the coefficient of friction to a level where the floss is easier to handle and does not slip through the fingers of the user as easily as the untreated floss. It has further been found that the thinner polytetrafluorethylene flosses of 600 to 800 denier that are coated with a friction enhancing coating are easy to handle and comfortable to use. The 600 to 800 denier flosses are particularly suitable for users having closely spaced teeth. Although the polytetrafluoroethylene has a very low coefficient of friction, it has been found that waxes and some other coating materials will adhere to the floss sufficiently to increase the coefficient of friction of the floss. It is believed that the ability of the friction coating to adhere to the floss is due in part to the porous nature of the expanded polytetrafluoroethylene.

The friction coating can be any substance that will adhere to the surface of the expanded polytetrafluoroethylene and which will increase the coefficient of friction of the expanded polytetrafluoroethylene surface to 0.08 or greater. Waxes will adhere to the surface of expanded polytetrafluoroethylene to a high degree. Polyvinylalcohol will also adhere to the surface of expanded polytetrafluoroethylene. If the substance itself will not sufficiently raise the coefficient of friction, it can carry an additive which will increase the coefficient of friction. The objective is to adhere a material to the expanded polytetrafluoroethylene surface so that the coefficient of friction can be increased to a desired level to improve the handling characteristics.

In this regard waxes are effective. A variety of waxes can be used. This includes naturally occurring and synthetic waxes. Petroleum derived waxes, such as paraffin and microcrystalline waxes, can be used. A suitable wax should have a melting point of greater than about 50° C. and should be plastic and pliable at room temperature. The wax shoud not be brittle at room temperature. These latter requirements negate the use of some waxes. Waxes that melt at less than about 50° C. can become molten during product storage and cause the wax on the floss strands to flow. This could result in problems in dispensing the floss from the rolls. Also if the melting point of the wax is around 40° C., the coating could end up being a lubricant at room and body temperatures if it becomes a liquid. This would then lower the coefficient of friction of the strand during usage rather than raise the coefficient of friction. In addition, if the wax is brittle the wax will crack and become removed from the floss during processing and packaging, and later during dispensing and handling prior to usage. Thus, essentially any wax can be used as long as it has a melting point greater than about 50° C. and the wax is not brittle at room temperature, i.e., about 25° C. It also should not be tacky at room temperature.

In the preferred embodiments of the invention, the friction coating is a microcrystalline wax. Microcrystalline waxes are well known in the art. The preferred microcrystalline waxes have a molecular weight of about 500 g/mole to about 900 g/mole and preferably about 600 g/mole to about 800 g/mole. Such microcrystalline waxes have a melting point of about 50° C. to about 100° C. and preferably about 60° C. to about 80° C. Alternative coating materials may include for example a water soluble coating such as polyvinyl alcohol or polyethyleneoxide. These can also be used in addition to a wax coating. The friction enhancing coating may be any coating material that is able to adhere to the polytetrafluoroethylene floss to increase the coefficient of friction. Preferably the coating material is sufficiently soft whereby the coating can be easily scraped off during the initial use of the floss to expose the polytetrafluoroethylene.

Microcrystalline waxes which can be used in the present invention include those sold under the tradenames Ultraflex (mp 65.6° C.), Victory (mp 78.9° C.), Be Square 175 (mp 83.9° C.), Starwax (mp 85.6° C.), Be Square 185 (mp 87.8° C.), Be Square 195 (mp 92.2° C.), Petrolite C-700 (mp 92.2° C.) and Petrolite C-1035 (mp 93.3° C.) by Petrolite Corporation of Tulsa, Okla. Other microcrystalline waxes which may be used include, for example, those sold by Boler Petroleum Company of Wayne, Pa. under the tradename Bowax 1018 (mp 68.3° C.), Mekon White (mp 93.3° C.) and Fortex (mp 96.1° C.). The preferred microcrystalline waxes are sold by Petrolite Corp. under the tradename Victory and by Witco under the tradename Witco 445, having a melting point of 78.9° C. and an average molecular weight of about 650 g/mole.

The molecular weights of waxes are calculated as the average of the molecular weights of their hydrocarbon constituents. Paraffin waxes are mainly composed of normal acyclic hydrocarbons and can frequently be characterized by their average molecular weights. It is more difficult to determine the molecular weight of the microcrystalline waxes which typically contain substantial amounts of secondary and tertiary acyclic hydrocarbon isomers and/or cyclic hydrocarbons. There is not necessarily a direct correlation between melting point and molecular weight of the microcrystalline waxes. Nevertheless, lower melting microcrystalline waxes generally have lower molecular weights.

The dental flosses are prepared from expanded polytetrafluoroethylene having a weight of about 100 denier to about 1500 denier. In one preferred form of the invention, the expanded polytetrafluoroethylene has a weight of about 600 denier to about 800 denier. As used herein, denier is intended to refer to the weight in grams of the strand per 9,000 meters. The weight of the strand in denier is proportional to the diameter of the strand and the extent of the expansion process. The flosses prepared from 600 denier to 800 denier strand are effective as flosses. In another preferred embodiment multiple strands of polytetrafluoroethylene of a denier of about 100 to 600 are formed into a single thread floss. This will consist of about 2 to 12 strands of expanded polytetrafluoroethylene depending on the denier. The strands are lightly twisted to produce a single thread. This will consist of about 1 to 5 twists per inch. In this case the friction-increasing coating will be a wax that will perform the function of binding the strands into a thread and also increase the coefficient of friction of the expanded polytetrafluoroethylene. The net result is a floss that has a multiple number of strands, but yet a lower coefficient of friction than conventional nylon flosses. The resulting thread has a denier of about 500 to about 1500 and preferably about 600 denier to about 1200 denier.

The tensile strength of the expanded polytetrafluoroethylene is generally at least about 10,000 psi. The polymeric matrix strength of the polytetrafluoroethylene is at least about 100,000 psi. It has been found that the relationship of the tensile strength of the expanded polytetrafluoroethylene and the weight in denier is not linear. Although the tensile strength decreases as the denier decreases, the expanded polytetrafluoroethylene at 500 to 600 denier has sufficient tensile strength to be used as a dental floss without breaking. The low coefficient of friction of the polytetrafluoroethylene minimizes the trauma and irritation of the floss against the gum tissue at a low floss weight. The low coefficient of friction of the polytetrafluoroethylene results in reduced friction against the tooth surface thereby allowing a thin floss of 600 or 800 denier to be used without breakage of the floss.

The wax or other friction coating may be applied to the expanded polytetrafluoroethylene floss by conventional techniques including, for example, spraying, padding and immersing in a molten or emulsion bath. In one embodiment of the invention, the wax is dispersed in a solvent or carrier as a bath. The strand is passed through the bath and dried to remove the solvent. The dried floss is then wound on a spool and packaged according to conventional procedures. In another embodiment the strand is passed through a molten wax bath. The strand picks up wax and exits the bath. On cooling there is produced an effective coating of the wax on the strand.

The wax or other friction coating applied to a multistrand material is likewise applied from either an emulsion or molten bath of wax. The multiple strand material is passed through this bath with a light twisting either before passing into the bath, while in the bath, or upon the exit from the bath. A light twisting is about 1 to 5 twists per inch.

The friction coating is applied to the expanded polytetrafluoroethylene floss at a coat weight to result in a floss having a friction coefficient of about 0.08 to about 0.25, preferably about 0.12 to about 0.20. The friction coating may contain suitable known additives to adjust the friction coefficient. It has been found that the expanded polytetrafluoroethylene coated with a wax to have a friction coefficient of 0.08 to 0.25 is able to be handled easily by the user and is able to slide easily between the teeth without injury to the gums. It is believed that during use, as the floss is passed through the tight spaces between the teeth, some of the wax coating is scraped from the floss to expose the polytetrafluoroethylene. The exposed polytetrafluoroethylene has a sufficiently low friction coefficient to inhibit injury to the gum tissue during use of the floss.

In a preferred form of the invention, the floss is provided with an active component such as, for example, a dentifrice or pharmacological component. The component may be dispersed in the friction coating, applied as a substrate coating before the friction coating, or as an outer coating over the friction coating. In the preferred embodiment, the active component is dispersed in a solvent or carrier with the friction coating and applied to the floss in a single coating step. Alternatively the active component is impregnated into the porous structure of the floss whereby the active component is released during use.

The dentifrice is preferably a fluoride or fluoride-containing compound such as sodium fluoride, potassium fluoride, ammonium fluoride, sodium difluoride, potassium difluoride, ammonium difluoride, sodium silicofluoride, zinc fluoride, and stannous fluoride. Other dentifrices include, for example, ureases, acid phosphates, calcium carbonate, and magnesium carbonate. Examples of the acid phosphates which may be used include, for example, orthophosphoric acid, monosodium phosphate, monopotassium phosphate, disodium phosphate, dipotassium phosphate, monoammonium phosphate, hemisodium phosphate and sodium hexametaphosphate salts. The dentifrice is preferably included in the floss in an amount sufficient to provide a topical concentration of about 5 to about 1000 ppm at the tooth surface.

Other active components which may be incorporated within the floss include hydrogen peroxide or peroxide producing components such as PVP $H_2O_2$ or Carbamide $H_2O_2$ Fluoride, tooth acidulating agents such as buffered or acidulated phosphofluoride, sodium monofluorophosphate, plaque control agents, tartar control agents, antibiotics to treat pyorrhea and gingivitis, teeth whitening and bleaching agents, pH buffering agents, antifungal agents, remineralizing agents, hemostatic agents, immunological agents and nonionic and cationic antibacterials such as benzothonium chloride, acetyl trimethyl ammonium bromide, sanguinaria, triclosan (nonionic), tetracycline, cetyl pyridinium chloride, and benzothonium chloride. When triclosan or a similar agent is used, preferably a Gantrez resin is also present. Gantrez resins are a product of GAF Corporation. Additional active components include vitamins, such as Vitamin A, surfactants and flavors including anise, peppermint, wintergreen, spearmint, fruit flavors and the like. Among the pharmacological active agents which may be included are, for example, anti-cancer agents, stimulants, bone growth agents, antigens, hormones, steroids, anti-inflammatory agents and analgesic agents. In a further embodiment, the active agent may be a coagulant to inhibit any bleeding which may be produced by flossing. Although the flosses of the present invention are less prone to cause bleeding than the conventional dental flosses, some bleeding may occur when the user has sensitive gingival tissue. Preferably, the coagulant is mixed in the wax coating so as to directly contact the gum tissue. The coagulants may include vitamin K, calcium ions in the form of water-soluble calcium salts and blood factors that initiate the coagulation cascade. It is possible to incorporate other coagulants from solution in finely dispersed form in the wax coating medium. Alternatively, the coagulants may be solubilized in non-toxic solvents, such as ethanol, polyethylene terephthalate, or diethyl ether. A preferred carrier for this purpose is a water-soluble type of resin, such as polyethylene glycol having an average molecular weight from about 4000 to about 6000 g/mole. The coagulating agents may be applied to the wax coating during or after the initial wax coating has dried. Additional active agents may include, for example, aminocaproic acid, tranexamic acid, adrenaline, alum, noradrenaline, iron salts, zinc salts and calcium alginate.

In further embodiments, dentally acceptable agents such as a cooling agent, for example, menthol and analogues such as N-ether-p-methane-3-carboxamide may be incorporated with the coated floss to help the patient to detect where the treatment has been applied. The floss may further incorporate colorant agents or fluorescent dye to identify residual plaque deposits, such as, for example, FD&C Red 3 and FD&C Red 4. Polishing agents such as hydrated amorphous silica, hydrated alumina, and calcium carbonate may be applied to the expanded polytetrafluoroethylene floss after the strand is formed.

The generally low coefficient of friction of the wax coated expanded polytetrafluoroethylene flosses of this invention gives them a significantly enhanced ability to glide easily between tight interproximal contact point areas. The low coefficient of friction of the polytetrafluoroethylene is less abrasive on the gingival tissue, enamel, dentin and cementum than most currently available dental floss. The wax coating generally appears to be easily removed from the floss as it passes between the interproximal dental contact points so that the remaining exposed expanded polytetrafluoroethylene floss slides without tending to cause substantial gingival bleeding. Moreover, the expanded polytetrafluoroethylene is about as strong as conventional flosses, but it is significantly more resistant to shredding and breaking.

The following examples demonstrate the ability of the wax coating on the expanded polytetrafluoroethylene to increase the coefficient of friction to a desirable level whereby the floss can easily be handled by a user. Unless otherwise indicated, the coefficient of friction is measured by the technique described by Scott & Robbins, J. Soc. Cosmet. Chem., 31, pages 179–200 (July/August, 1980). This technique, described for measuring friction of reference surfaces by particularly passing hair fibers through an immersed combing device and measuring the COF with Instron(TM) Tensile Tester, is suitable for COF measurement of dental floss with interstitial dental surfaces replacing the combing device.

EXAMPLE I

The example considers the ability to coat an expanded polytetrafluoroethylene fiber with a microcrystalline wax and its effect on the coefficient of friction. For comparative purposes, four commercially available nylon dental flosses identified as samples 1, 2, 3 and 4 were tested to determine the coefficient of friction. Four test samples of expanded polytetrafluoroethylene were obtained from W. L. Gore & Associates, Inc. The comparative test samples were about 1100 denier. Comparative sample 5 contained no particulate filler material. Comparative sample 6 contained 2.0% $TiO_2$, while comparative sample 7 contained 8.0% $TiO_2$. Additional samples of the expanded polytetrafluoroethylene were coated with a microcrystalline wax sold under the tradename Victory by Petrolite Corp. The expanded strands were coated by immersing the strands in a bath and drying the impregnated strands. The coefficient of friction for each sample is recorded in Table I.

TABLE I

| Sample | Composition | Coefficient of Friction |
|---|---|---|
| 1 | Waxed nylon (I) | 0.22930 |
| 2 | Unwaxed nylon | 0.21294 |
| 3 | Nylon (extra fine) | 0.20098 |
| 4 | Waxed nylon (II) | 0.15820 |
| 5 | Expanded PTFE | 0.06886 |
| 6 | Expanded PTFE with 2.0% $TiO_2$ | 0.07152 |
| 7 | Expanded PTFE with 8.0% $TiO_2$ | 0.07926 |
| 8 | Expanded PTFE with anti-tartar agent | 0.17455 |
| 9 | Waxed expanded PTFE with 8.0% $TiO_2$ and white oil | 0.08970 |
| 10 | Waxed expanded PTFE with flavoring agent | 0.09148 |
| 11 | Waxed expanded PTFE | 0.10352 |
| 12 | Waxed expanded PTFE with flavoring agent | 0.18080 |
| 13 | Waxed expanded PTFE with anti-tartar agent | 0.21605 |

The above data of Table 1 demonstrate that the commercial nylon flosses have a friction coefficient significantly higher than the expanded coated or uncoated PTFE. The expanded PTFE which was coated with the microcrystalline wax has a higher friction coefficient than the uncoated PTFE and is still lower than the conventional nylon floss.

EXAMPLE II

A selection of single strand expanded polytetrafluoroethylene flosses were consumer tested along with a commercially available multi-filament nylon floss. The test was a four week, blind, crossover study. The test panelists were all floss users and used floss at least three times per week. During the study the test floss had to be used at least three times per week. The correlations of the test panel data is set out in following Table II and Table III. The flosses were rated by the panelists according to their overall preference.

TABLE II

|  | 600 D | 800 D | 1200 D | Nylon Floss* |
|---|---|---|---|---|
| Like Better Than | 13 | 17 | 17 | 9 |
| Like the same as | 16 | 20 | 21 | 18 |
| Like less than their regular floss | 15 | 6 | 6 | 19 |

*Johnson & Johnson Co.

TABLE III

|  | 600 D | 800 D | 1200 D | Nylon Floss* |
|---|---|---|---|---|
| Like a lot | 10 | 15 | 17 | 7 |
| Like somewhat | 11 | 13 | 18 | 11 |
| Neither like nor dislike | 10 | 12 | 5 | 9 |
| Dislike somewhat | 13 | 4 | 5 | 10 |
| Dislike a lot | 1 | 1 | 1 | 6 |

*Johnson & Johnson Co.

The data illustrates that 600 denier, 800 denier and 1200 denier expanded polytetrafluoroethylene single strand floss is preferred as compared to a conventional nylon multi-filament floss. Of the expanded polytetrafluoroethylene flosses, the 800 denier and 1200 denier flosses are preferred.

What is claimed is:

1. A dental cleaning floss comprising at least one polytetrafluoroethylene strand that has been expanded by stretching under conditions to increase the tensile strength thereof, said floss having a coating of at least one material capable of increasing the coefficient of friction, wherein said dental floss has a denier of about 500 to 1500 and a coefficient of friction of about 0.08 to about 0.25.

2. The dental floss of claim 1 wherein said floss comprises a plurality of polytetrafluoroethylene strands, each strand being of a denier of 100 to 600.

3. The dental floss of claim 1 wherein said floss comprises a single polytetrafluoroethylene strand of about 600 denier to about 1200 denier.

4. The dental floss of claim 1 wherein said coating is a wax which has a melting point of at least about 50° C. and is not brittle at about 25° C.

5. The dental floss of claim 4 wherein said wax is a microcrystalline wax having a melting point of about 60° C. to 80° C.

6. The dental floss of claim 1 wherein said coating is selected from the group consisting of microcrystalline wax, polyvinyl alcohol and polyethyleneoxide.

7. The dental floss of claim 1 wherein said floss has a coefficient of friction of about 0.15 to about 0.20.

8. The dental floss of claim 1 wherein the polytetrafluoroethylene strand includes at least one active material selected from the group consisting of remineralizing agents, whitening agents, antibiotic agents, antifungal agents, immunological agents, anti-tartar agents, anti-caries agents, anti-plaque agents, lysozymes, antibacterial agents, anti-inflammatory agents, hemostatic agents, analgesics and mixtures thereof.

9. The dental floss of claim 8 wherein said active agent is selected from the group consisting of sodium fluoride, zinc chloride, tetrasodium pyrophosphate, sodium acid pyrophosphate, tetrapotassium pyrophosphate, vitamin K, water soluble calcium salts, blood factors that initiate the coagulation cascade, aminocaproic acid, tranexamic acid, adrenaline, alum, noradrenaline, iron salts and calcium alginate, sodium monofluorophosphate, stannous fluoride, chlorhexidine, hexachlorophene, cetyl pyridinium chloride, benzethonium chloride, ureases, calcium carbonate, magnesium carbonate, othophosphoric acid, monosodium phosphate, monopotassium phosphate, disodium phosphate, dipotassium phosphate, hemisodium phosphate, benzothonium chloride, acetyl trimethyl ammonium bromide, sanguinaria, triclosan, tetracycline, cetyl pyridinium chloride, benzothonium chloride and mixtures thereof.

10. A dental cleaning floss comprising a thread formed from a plurality of polytetrafluoroethylene strands that have been expanded by stretching at an elevated temperature, said floss including at least one material capable of increasing the coefficient of friction of said polytetrafluoroethylene, wherein said dental floss has a denier of about 500 to 1500 and a coefficient of friction of about 0.08 to about 0.25.

11. The dental floss of claim 10 wherein said polytetrafluoroethylene strands are from about 100 denier to about 600 denier and are twisted to form said thread.

12. The dental floss of claim 11 wherein said thread is formed from about two to twelve polytetrafluoroethylene strands and are twisted about one to five turns per inch.

13. The dental floss of claim 10 wherein said material capable of increasing the coefficient of friction is selected from the group consisting of wax having a melting point of at least about 50° C., polyvinyl alcohol and polyethylene oxide.

14. The dental floss of claim 13 wherein said wax is microcrystalline wax.

15. A dental cleaning floss comprising at least one polytetrafluoroethylene strand that has been expanded by stretching under conditions to increase the tensile strength thereof, said floss having a coating of at least one material capable of increasing the coefficient of friction, wherein said dental floss has a denier of about 500 to 1500 and a coefficient of friction of about 0.08 to about 0.25.

16. The dental floss of claim 15 wherein said strand has a tensile strength of at least about 10,000 psi.

17. The dental floss of claim 16 wherein said coating is selected from group consisting of wax, polyvinyl alcohol and polyethylene oxide.

18. The dental floss of claim 15 wherein said coating is wax having a melting point of about 50° C. and is not brittle at 25° C.

19. The dental floss of claim 15 wherein said coating is microcrystalline wax.

20. The dental floss of claim 15 wherein said floss includes at least one bioactive component.

* * * * *

(12) EX PARTE REEXAMINATION CERTIFICATE (6053rd)
United States Patent
Curtis et al.

(10) Number: US 5,209,251 C1
(45) Certificate Issued: Dec. 18, 2007

(54) DENTAL FLOSS

(75) Inventors: John P. Curtis, Bloomsbury, NJ (US); James H. Kemp, North Brunswick, NJ (US)

(73) Assignee: Colgate-Palmolive Company, Piscataway, NJ (US)

Reexamination Request:
No. 90/003,885, Jun. 30, 1995

Reexamination Certificate for:
Patent No.: 5,209,251
Issued: May 11, 1993
Appl. No.: 07/729,834
Filed: Jul. 11, 1991

Related U.S. Application Data

(63) Continuation-in-part of application No. 07/282,962, filed on Dec. 2, 1988, now Pat. No. 5,033,488, which is a continuation-in-part of application No. 07/174,757, filed on Mar. 29, 1988, now abandoned.

(51) Int. Cl.
*A61C 15/00* (2006.01)
*A61C 15/04* (2006.01)
*A61Q 11/00* (2006.01)

(52) U.S. Cl. ........................................................ 132/321
(58) Field of Classification Search ....................... None
See application file for complete search history.

(56) References Cited

U.S. PATENT DOCUMENTS

| | | | | |
|---|---|---|---|---|
| 2,700,636 A | * | 1/1955 | Ashton ......................... | 424/54 |
| 3,538,230 A | * | 11/1970 | Pader et al. .................. | 424/50 |
| 3,699,979 A | * | 10/1972 | Muhler et al. ............... | 132/321 |
| 3,734,081 A | | 5/1973 | Schaack | |
| 3,771,536 A | * | 11/1973 | Dragan ......................... | 132/321 |
| 3,800,812 A | * | 4/1974 | Jaffe ............................. | 132/321 |
| 3,830,246 A | * | 8/1974 | Gillings ....................... | 132/321 |
| 3,837,351 A | * | 9/1974 | Thornton ...................... | 132/321 |
| 3,897,795 A | * | 8/1975 | Engel ........................... | 132/321 |
| 3,943,949 A | * | 3/1976 | Ashton et al. ............... | 132/321 |
| 3,953,566 A | * | 4/1976 | Gore ............................ | 264/288 |
| 3,962,153 A | * | 6/1976 | Gore ............................ | 260/2.5 |
| 4,029,113 A | * | 6/1977 | Guyton ........................ | 132/321 |
| 4,033,365 A | * | 7/1977 | Klepak et al. ............... | 132/321 |
| 4,187,390 A | * | 2/1980 | Gore ............................ | 174/102 |
| 4,215,478 A | * | 8/1980 | Thomas et al. ............... | 433/25 |
| 4,256,806 A | * | 3/1981 | Snyder ......................... | 428/378 |
| 4,304,245 A | | 12/1981 | Lichfield | |
| 4,385,093 A | * | 5/1983 | Hubis .......................... | 428/316 |
| 4,414,990 A | * | 11/1983 | Yost ............................ | 132/321 |
| 4,478,665 A | * | 10/1984 | Hubis .......................... | 156/229 |
| 4,645,662 A | * | 2/1987 | Nakashima et al. .......... | 424/50 |
| 4,776,358 A | * | 10/1988 | Lorch .......................... | 433/216 |
| 4,836,226 A | | 6/1989 | Wolak | |
| 4,996,056 A | | 2/1991 | Blass | |

FOREIGN PATENT DOCUMENTS

| | | |
|---|---|---|
| EP | 0 080 440 | 6/1983 |
| EP | 0 136 727 A1 | 4/1985 |
| EP | 0 335 466 | 10/1989 |
| EP | 335466 * | 10/1989 |
| GB | 1380032 | 1/1975 |

OTHER PUBLICATIONS

Chemical Abstracts, vol. 97, 1992, p. 352, –97:11651e

\* cited by examiner

*Primary Examiner*—Beverly M. Flanagan

(57) ABSTRACT

A dental floss is produced from expanded polytetrafluoroethylene that has been coated with a friction enhancing coating such as a microcrystalline wax to increase the friction coefficient of the floss. The polytetrafluoroethylene is preferably expanded to form a structure having a plurality of nodes interconnected by fibrils. The floss has a tensile strength of at least about 10,000 psi and a weight of about 500 denier to about 1500 denier. The coefficient of friction of the wax coated floss ranges from about 0.08 to 0.25. The floss may be comprised of a single strand or multiple strands. The floss may contain an optional dentifrice or pharmaceutically active material for delivery to the tooth and gum surfaces during use.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, line 24:

Figure 1:
*FIG. 1 is a scanning electron microscopy (SEM) picture of the Expanded PTFE floss in virgin (uncoated) form at 1000 magnification, particularly showing the floss as being composed of a plurality of filaments. The projection on the right side of the picture is the outer surface of the floss which is separated from the interior to thereby expose the multi-filamentous nature of the interior.*
Figure 2:
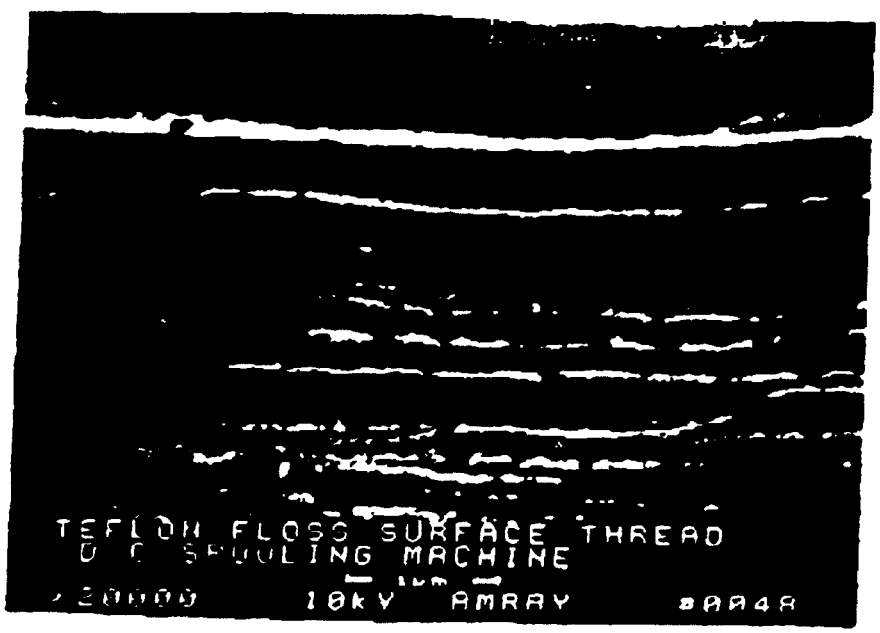
*FIG. 2 is an SEM picture of a portion of the Expanded PTFE interior of FIG. 1 at 20000 magnification particularly showing the porous nature of the Expanded PTFE.*
Figure 3:
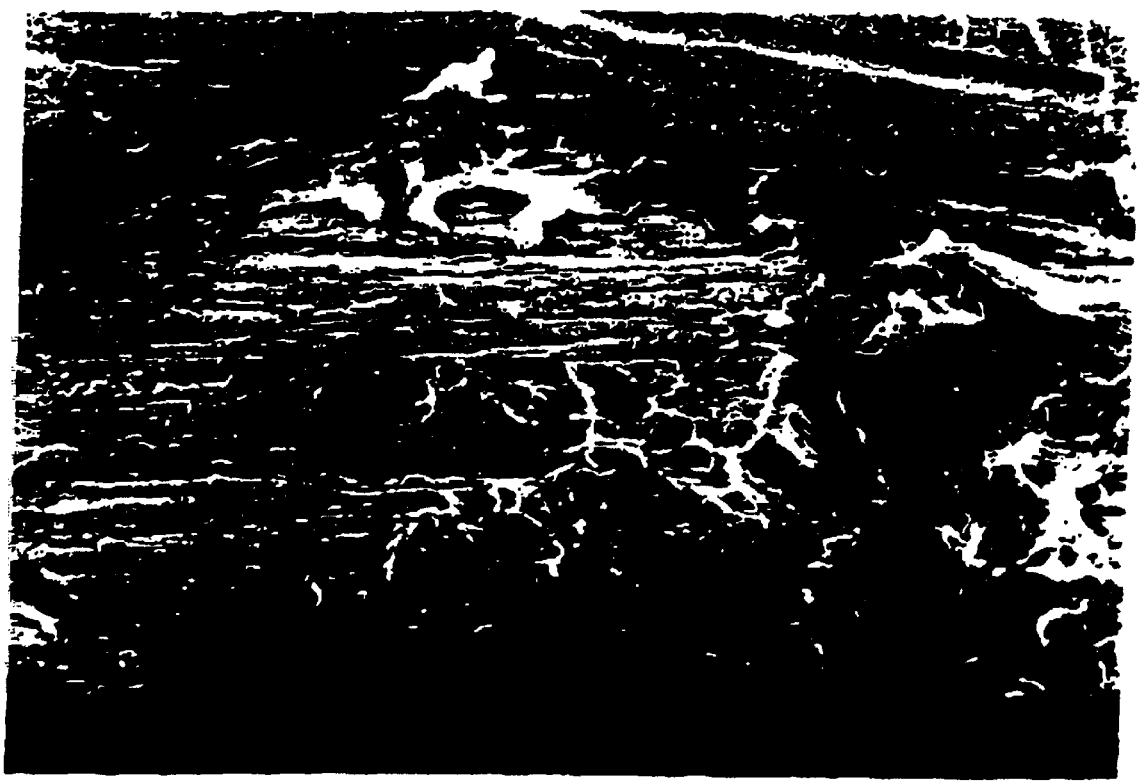
*FIG. 3 is an SEM picture of the Expanded PTFE surface having an MCW coating thereon at 500 magnification, particularly showing the non-continuous nature of the MCW coating, which is coated from an immersion bath onto the floss surface.*
Figure 4:
*FIG. 4 is an SEM picture at 500 magnification showing particles of flavor post-added by dusting over an MCW coating on the surface of Expanded PTFE, both of which appear in the background.*

*As an alternative embodiment to FIG. 4, the flavor may be incorporated on the floss by adding spray dried flavor to the MCW and coating the mixture on floss by immersing the floss in a bath of the mixture. As an additional alternative, the floss may be treated first by immersing it in a flavor bath and then post-coating with a bath of MCW.*

*As further alternatives to FIG. 4, flavor can be replaced or combined with actives such as anti-plaque, anti-caries and/or anti-tartar actives or other dentally acceptable agents.*

THE DRAWING FIGURES HAVE BEEN CHANGED AS FOLLOWS:

FIGS. 1–4 added.

AS A RESULT OF REEXAMINATION, IT HAS BEEN DETERMINED THAT:

Claims 1-20 are cancelled.

New claims 21-24 are added and determined to be patentable.

*21. A dental cleaning floss comprising at least one polytetrafluoroethylene strand that has been expanded by stretching under conditions to increase the tensile strength thereof, said floss having a microcrystalline wax coating which increases the coefficient of friction to facilitate flossing, wherein said dental floss has a denier of about 500 to 1500 and a coefficient of friction of about 0.08 to about 0.25.*

*22. A dental cleaning floss comprising at least one polytetrafluoroethylene strand that has been expanded by stretching under conditions to increase the tensile strength thereof, said floss having a microcrystalline wax coating which increases the coefficient of friction sufficiently high to permit the user to securely grasp the floss, wherein said dental has a denier of about 500 to 1500 and a coefficient of friction of about 0.08 to about 0.25.*

*23. The dental cleaning floss of any one of claims 21 or 22 further comprising at least one active material selected from the group consisting of an anti-tartar active, an anti-caries active, anti-plaque active, an anti-gingivitis active and a coagulating agent.*

*24. The dental cleaning floss of any one of claims 21 or 22 further comprising a flavor.*

\* \* \* \* \*